(12) United States Patent
Hong et al.

(10) Patent No.: US 8,073,547 B2
(45) Date of Patent: Dec. 6, 2011

(54) GUIDING APPARATUS AND METHOD FOR COCHLEAR IMPLANT

(75) Inventors: Sung-Hwa Hong, Seoul (KR); Sun-I Kim, Seoul (KR); In-Young Kim, Seoul (KR); Sang-Min Lee, Seoul (KR); See-Youn Kwon, Seoul (KR)

(73) Assignee: Hanyang Hak Won Co., Ltd., Seoul (KR)

( * ) Notice: Subject to any disclaimer, the term of this patent is extended or adjusted under 35 U.S.C. 154(b) by 1519 days.

(21) Appl. No.: 11/331,530

(22) Filed: Jan. 13, 2006

(65) Prior Publication Data

US 2006/0167472 A1 Jul. 27, 2006

Related U.S. Application Data

(63) Continuation of application No. PCT/KR03/02843, filed on Dec. 26, 2003.

(30) Foreign Application Priority Data

Jul. 14, 2003 (KR) .................. 10-2003-0047901

(51) Int. Cl.
*A61N 1/00* (2006.01)

(52) U.S. Cl. ...................................... 607/57

(58) Field of Classification Search ............. 607/55–57, 607/136–137, 115–116; 606/129; 600/101, 600/104, 117, 118
See application file for complete search history.

(56) References Cited

U.S. PATENT DOCUMENTS

| | | | | |
|---|---|---|---|---|
| 5,172,225 A | * | 12/1992 | Takahashi | 348/74 |
| 5,394,865 A | * | 3/1995 | Salerno | 600/199 |
| 5,400,771 A | * | 3/1995 | Pirak et al. | 600/109 |
| 5,419,312 A | * | 5/1995 | Arenberg et al. | 600/108 |
| 5,545,219 A | | 8/1996 | Kuzma | |
| 5,951,461 A | * | 9/1999 | Nyo et al. | 600/118 |
| 6,163,729 A | | 12/2000 | Kuzma | |
| 6,195,586 B1 | | 2/2001 | Kuzma | |
| 2002/0156513 A1 | * | 10/2002 | Borkan | 607/117 |
| 2004/0122501 A1 | * | 6/2004 | Dadd et al. | 607/137 |
| 2004/0147825 A1 | * | 7/2004 | Milojevic et al. | 600/372 |
| 2004/0243212 A1 | * | 12/2004 | Dadd et al. | 607/137 |
| 2006/0235500 A1 | * | 10/2006 | Gibson et al. | 607/137 |

FOREIGN PATENT DOCUMENTS

WO    WO 97/22313    6/1997

* cited by examiner

*Primary Examiner* — Eric D. Bertram
*Assistant Examiner* — Roland Dinga
(74) *Attorney, Agent, or Firm* — Knobbe, Martens, Olson & Bear LLP

(57) ABSTRACT

A guiding apparatus and a method for cochlear implant are disclosed. In one embodiment, the guiding apparatus for cochlear implant comprises i) an optical tube for transmitting an optical signal, ii) an optical signal emitting module for converting an electrical signal into the optical signal and emitting the optical signal through another end of the optical tube, iii) an optical signal detecting module for receiving the optical signal that is reflected by an obstacle or an inner wall of cochlear through another end of the optical tube and converting the received optical signal into an electrical signal and iv) a central processor for analyzing optical emission energy information and optical detection energy information to generate inserting route information. According to one embodiment, it is possible to decrease injuries to the inner wall of a cochlear canal and optimize the position of an electrode to be inserted into the cochlear canal.

12 Claims, 4 Drawing Sheets

GUIDING APPARATUS AND METHOD FOR COCHLEAR IMPLANT

RELATED APPLICATIONS

This application is a continuation application, and claims the benefit under 35 U.S.C. §§ 120 and 365 of PCT Application No. PCT/KR2003/002843, filed on Dec. 26, 2003 and published on Jan. 20, 2005, in English, which is hereby incorporated by reference.

BACKGROUND OF THE INVENTION

1. Field of the Invention

The present invention relates to a guiding apparatus and a method for cochlear implant, more particularly, for reducing injuries caused by an electrode to an inner wall of the cochlear canal during insertion and enabling the electrode to be properly located.

2. Description of the Related Technology

The cochlear, a human organ for the sense of hearing, looks like a snail-shaped tube having a length of about 3.5 cm and two and half turns.

And the cochlear implant system is a device for electrically stimulating auditory nerves of a patient who is profoundly deaf or severely hard of sensorineural hearing due to the injuries on a Corti organ in the inner ear or a deafness to deliver the signals to the cerebrum. That is, the cochlear implant system for sensorineural hearing loss or deafness converts sound into a weak electrical signal by use of a small-sized computer and provides the electrical signal directly to the auditory nerves according to a magnitude and a tone to deliver the sound to the cerebrum.

In 1967, professor Graeme Clark of Melbourne University started to study a hearing aid, and as many studies executed after 10-channel hearing aid had been transplanted to the first patient in 1978, there are about 50,000 cases until now.

The cochlear implant device has internally-implanted and external portion. The external component, being located at the outside, includes a microphone, a voice processor and an external coil. After processing a voice signal (i.e., sound) received by the microphone at the voice processor, the processed signal and a power for operating internal circuit are sent to the internally-implanted portion through the external coil.

The internally-implanted portion, being transplanted into the body, includes an internal circuit with a circuit and a stimulation chip, a package for sealing to protect the internal circuit from humoral materials and/or ions, an electrode to be inserted into the cochlear, and an internal coil for remotely controlling the stimulation chip and receiving the processed signal from the outside. The internal circuit, the package, the electrode and the internal coil are electrically coupled to each other. The signal from the external coil is received by the internal coil, and separated into a power signal to be used to operate itself and a nerve ganglion cell stimulation signal, which stimulates the nerve ganglion cell in the cochlear though the electrode so that the stimulated cell generates the electrical signal to be delivered to the brain via auditory nerve. By way of this, one who has difficulty in hearing or deafness can hear.

In an operation method for the cochlear implant system, the mastoid of a patient is grinded to expose the oval window of a cochlear canal where the electrode will be inserted and the very thin and long electrode that is about 10 mm in thickness and about 2~2.5 cm in length is inserted into the cochlear canal.

Hereinafter, the conventional method for inserting the cochlear implant system will be briefly described with reference to FIG. 1 and FIG. 2.

FIG. 1 is a block diagram of the conventional device for inserting the cochlear implant system, and FIG. 2 shows a method for inserting the cochlear implant system.

Referring to FIG. 1 and FIG. 2, the conventional device comprises an electrode 110 and a guiding wire 120.

In the conventional method, a surgeon inserts the guiding wire 120, so-called stylet, into the electrode at step 150, and then selects a proper position in the cochlear canal based on his operation experiences and tactical sense at step 155. After locating the electrode 110 on the proper position at step 160, the electrode 110 is fixed in the cochlear canal by removing the guiding wire 120 at step 165.

In addition, a subsidiary (not shown) can be inserted into the cochlear canal and then the electrode can be inserted.

In the conventional technique, the electrode 110 has a curved shape in itself (not shown) and is maintained a straight line during insertion by the guiding wire 120 or the subsidiary for easy insertion. And, by removing the guiding wire 120 after inserting the electrode 110, the safe installation of the electrode in the cochlear canal and the easiness of operation can be accomplished.

But, since the conventional method is depending entirely on a surgeon's tactile sense, it is very difficult and complicated to insert the electrode.

Also, in the conventional method, there is a possibility to cause tissue injuries when inserting the cochlear implant system into the cochlear canal.

Furthermore, although the more the electrode is close to the central axis wall of a cochlear the more stimulation is effective in the conventional method, it is impossible to get information about the inserting route and the position of the electrode during the operation.

SUMMARY OF CERTAIN INVENTIVE ASPECTS

One aspect of the invention provides a guiding apparatus and method for cochlear implant, which provide information of a route and position to a surgeon such that injuries to the inner wall of cochlear canal can be decreased and the optimized position of an electrode can be accomplished.

Another aspect of the invention provides a guiding apparatus and method for cochlear implant, which can detect obstacles on the inserting route by use of the reflected optical signals and remove the detected obstacles by use of a laser beam.

Another aspect of the invention provides a guiding apparatus and method for cochlear implant, which can increase the accuracy and safety of operation by providing a numerical and visualized information of the inserting process and route by use of optical signals.

Another aspect of the present invention provides a guiding apparatus for cochlear implant, which provides information on an inserting route of a cochlear implant system, comprising: i) at least one optical tube for transmitting an optical signal, ii) an optical signal emitting module, coupled to one end of the optical tube, for converting an electrical signal into the optical signal and emitting the optical signal through another end of the optical tube, iii) an optical signal detecting module, coupled to one end of the optical tube, for receiving the optical signal that is reflected by an obstacle or an inner wall of cochlear through another end of the optical tube and converting the received optical signal into an electrical signal, iv) a central processor for providing a control signal to the optical signal emitting module and the optical signal detecting module and analyzing optical emission energy information from the optical signal emitting module and optical detection energy information from optical signal detecting module to generate inserting route information and v) a display for output inserting route information.

In one embodiment, the central processor comprises an analysis processor for analyzing optical emission energy information and optical detection energy information to generate inserting route information of the cochlear implant system, wherein inserting route information comprises at least one of route information of an inner wall of a cochlear canal and position information of the optical tube, and a transmittance controller for generating and transmitting a control signal to control an amount of optical emission energy to the optical signal emitting module and a control signal to control the detection of optical signal to the optical signal detecting module.

In one embodiment, the optical signal emitting module comprises an amplifier for amplifying the electrical signal in the form of a pulse from the central controller, a modulator for converting the amplified signal into the optical signal by use of an optical diode, and an illuminator for controlling an radiation angle of an optical signal by use of an optical device.

In one embodiment, the optical signal detecting module comprises a collector for detecting the optical signal reflected by the inner wall of cochlear canal or the obstacle by use of an optical detecting sensor, a converter for converting the detected optical signal into the electrical signal, and an amplifier for amplifying the electrical signal to be sent to the central processor.

In one embodiment, the guiding apparatus for cochlear implant further comprises a contact switch for connecting one end of the optical tube to one of the optical signal emitting module or the optical signal detecting module under the control of the transmittance controller in the case of one optical tube available.

In one embodiment, the optical tube that is made of glass or plastic material is in the form of a thin line, and the optical signal emitting module and the optical signal detecting module are connectable to separate optical tubes respectively. In one embodiment, an electrode can contain the optical tube for working as a stylet for supporting the insertion of the electrode into the cochlear canal or as an endoscope for detecting an existence of obstacle.

In one embodiment, the guiding apparatus for cochlear implant further comprises an optical signal magnitude switch for inputting a command for generating an optical laser for removing the obstacle, wherein the central process in accordance to the command controls the optical signal emitting module to amplify the optical signal to generate the optical laser and the optical laser is emitted through the one end of the optical tube toward the obstacle.

In one embodiment, the guiding apparatus for cochlear implant further comprises an emission control switch for inputting a command for selecting continuous emission or intermittent emission.

Another aspect of the present invention provides a guiding method for cochlear implant with using inserting route information of a cochlear implant system, comprising: i) emitting an optical signal through one end of an optical tube or an electrode after converting an electrical signal into the optical signal, ii) detecting an optical signal reflected by an inner wall of cochlear canal or an obstacle through one end of the optical tube or the electrode, iii) generating inserting route information of the cochlear implant system by comparing an optical emission energy of the emitted optical signal and an optical detection energy of the detected optical signal, iv) outputting inserting route information on display; receiving an optical laser generation command if the obstacle exists ahead of the optical tube or the electrode and v) removing the obstacle by emitting the optical laser.

In one embodiment, the guiding method for cochlear implant further comprises installing the electrode in the cochlear canal by removing the optical tube when the electrode contains the optical tube and the electrode reaches the predetermined position through an inner ear.

DETAILED DESCRIPTION OF CERTAIN INVENTIVE EMBODIMENTS

Hereinafter, embodiments of the present invention will be described with accompanying drawings.

Figure 3:
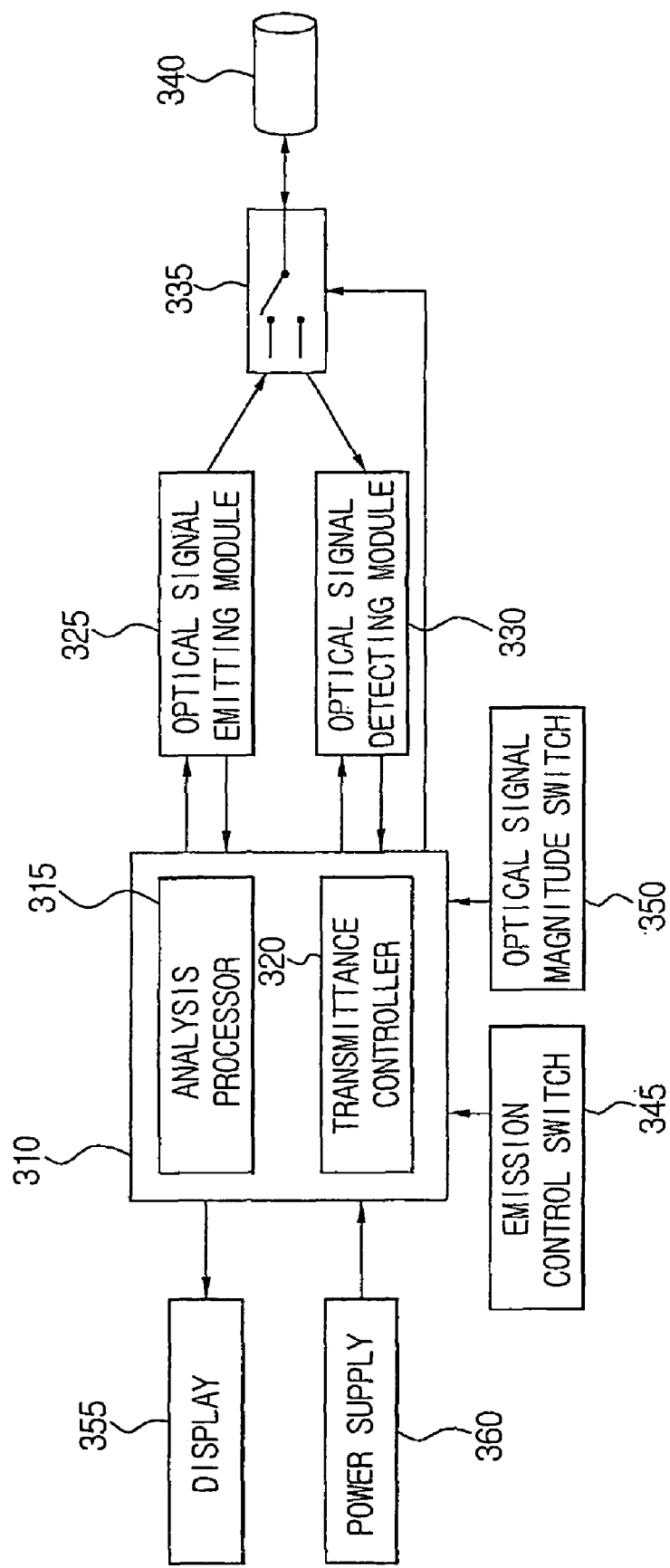
FIG. 3 is a block diagram of the guiding apparatus for cochlear implant according to one embodiment of the present invention.

FIG. 3 is a block diagram of the guiding apparatus for cochlear implant according to one embodiment of the present invention.

Referring to FIG. 3, the guiding apparatus for cochlear implant according to one embodiment of the present invention comprises a central processor 310, an optical signal emitting module 325, an optical signal detecting module 330, a contact switch 335, an optical tube 340, an emission control switch 345, an optical signal magnitude switch 350, a display 355, and a power supply 360.

The central processor 310 comprises an analysis processor 315 and a transmittance controller 320. The analysis processor 315 compares optical emission/detection energy in the optical signal emitting module 325 and optical signal detecting module 330 and analyzes route information of inner wall of cochlear canal and position information of optical tube 340. Also, the analysis processor 315 further generates visualized information by use of analyzed information. By the functions of the analysis processor 315, obstacles or cochlear wall that may exist ahead of the optical tube 340 or electrode 110 coupled to the optical tube 340 can be detected. The transmittance controller 320 controls the signal generation of the optical signal emitting module 325 and optical signal detecting module 330.

The optical signal emitting module 325 converts an electrical signal into an optical signal and emits the optical signal under the control of the transmittance controller 320, and sends optical emission energy information to the analysis processor 315. The optical signal emitting module 325 comprises an amplifier for amplifying the electrical signal in the form of pulse from the transmittance controller 320, a modulator for converting the amplified signal into the optical signal, and an illuminator for controlling an radiation angle by use of optical device.

The optical signal detecting module 330 detects the optical signal being reflected by the inner wall of cochlear canal and converts the detected signal into corresponding electrical signal under the control of the transmittance controller 320, and sends optical detection energy information to the analysis processor 315. The optical signal detecting module 330 comprises a collector for detecting the optical signal (i.e. receiving and desynchronizing the optical pulse signal emitted by the optical emitting module 325) reflected by the inner wall of cochlear canal by use of an optical detecting sensor, a converter for converting the detected optical signal into an electrical signal, and an amplifier for amplifying the electrical signal to be sent to the analysis processor 315. It is preferable to use an optical sensor with high sensitivity as optical detecting sensor.

The contact switch 335 connects the optical tube to the optical signal emitting module 325 or the optical signal detecting module 330 under the control of transmittance controller 320 if one or more optical tubes are connectable to the optical signal emitting module 325 and the optical signal detecting module 330. That is, the contact switch is a chopper for selecting optical route for optical signal emission and detection when one optical tube 340 is used.

Figure 1:
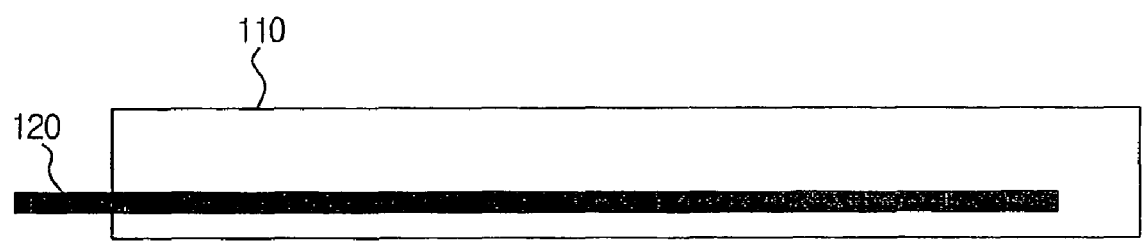
FIG. 1 is a block diagram of the conventional device for inserting the cochlear implant system.
Figure 2:
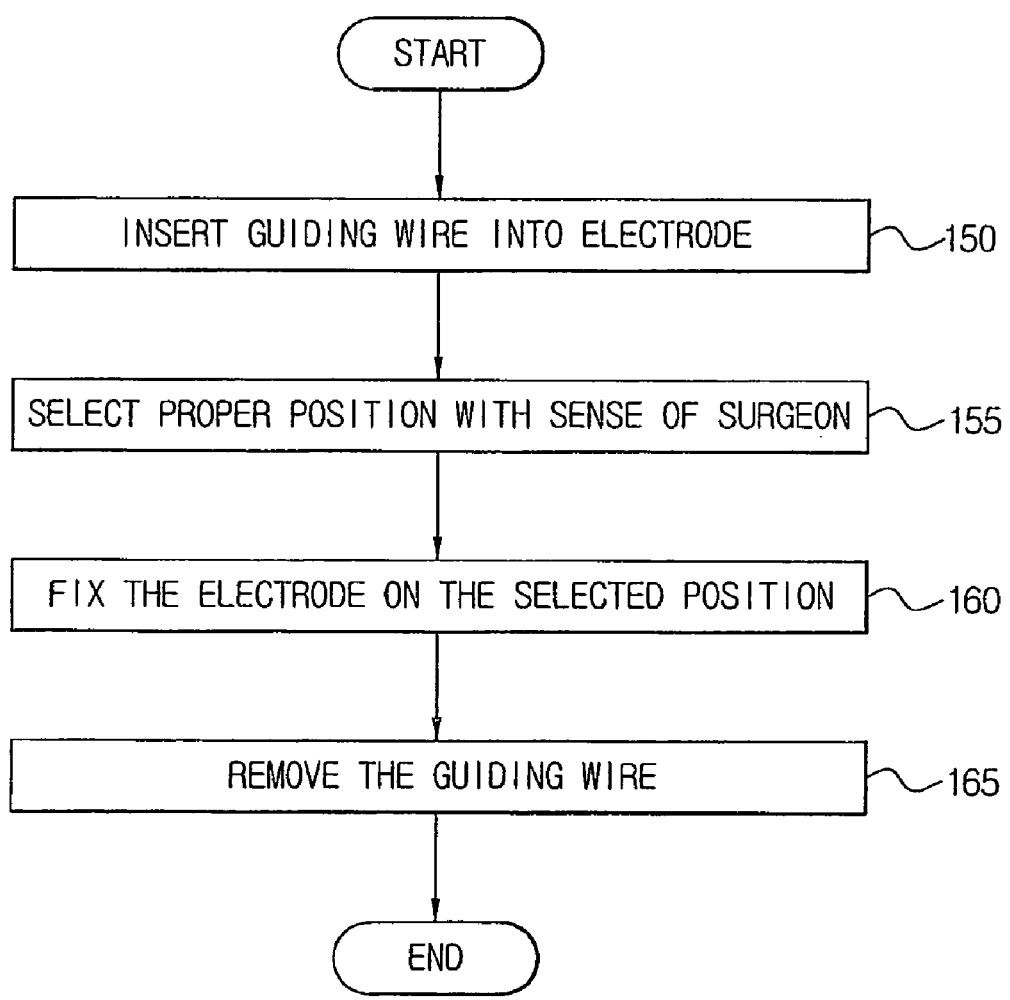
FIG. 2 shows a conventional method for inserting the cochlear implant system.

The optical tube 340 comprises all optical signal transmission medium in the form of thin line, which is made of glass or plastic material. The optical tube 340 works as a guiding wire, i.e., stylet for supporting the insertion of electrode as described in FIG. 1, and can be used as an endoscope when it is not coupled to the electrode 110. The optical tube 340 can be in the form of bundle consisting of one or more optical tubes. For example, in the case of one optical tube 340, the emission process is performed when the optical signal emitting module 325 is connected to the optical tube 340 by the operation of the contact switch 335, and the detection process is performed by the operation of the contact switch 335 when the optical signal detecting module 330 is connected to the optical tube 340. Of course, if plural optical tubes are used and each one is connected to the optical signal emitting module 325 and optical signal detecting module 330 respectively, the contact switch 335 will be omitted.

The emission control switch 345 is an input device for surgeon to control the emission and detection of the optical signal to be continuously or intermittently performed. The optical signal magnitude switch 350 is an input device for surgeon to control the magnitude of optical beam to be emitted from the optical signal emitting module 325. For example, the emission control switch 345 and the optical signal magnitude switch 350 can be implemented as an input switch.

The display 355 displays the analysis result of the analysis processor 315 such as route information, position information, etc, by means of numerical information and/or visualized information.

In one embodiment, the power supply 360 provides electrical power required to operate the guiding apparatus for cochlear implant.

Also, although it is not shown in FIG. 3, the guiding apparatus for cochlear implant further comprises a mode switch for selecting one from an inspection mode and a treatment mode. For example, after selecting the inspection mode, the surgeon can inspect obstacles on the step of inserting optical tube into the cochlear of patient, and if there exists an obstacle, then burn out the obstacle with the optical laser after changing to the treatment mode.

Figure 4:
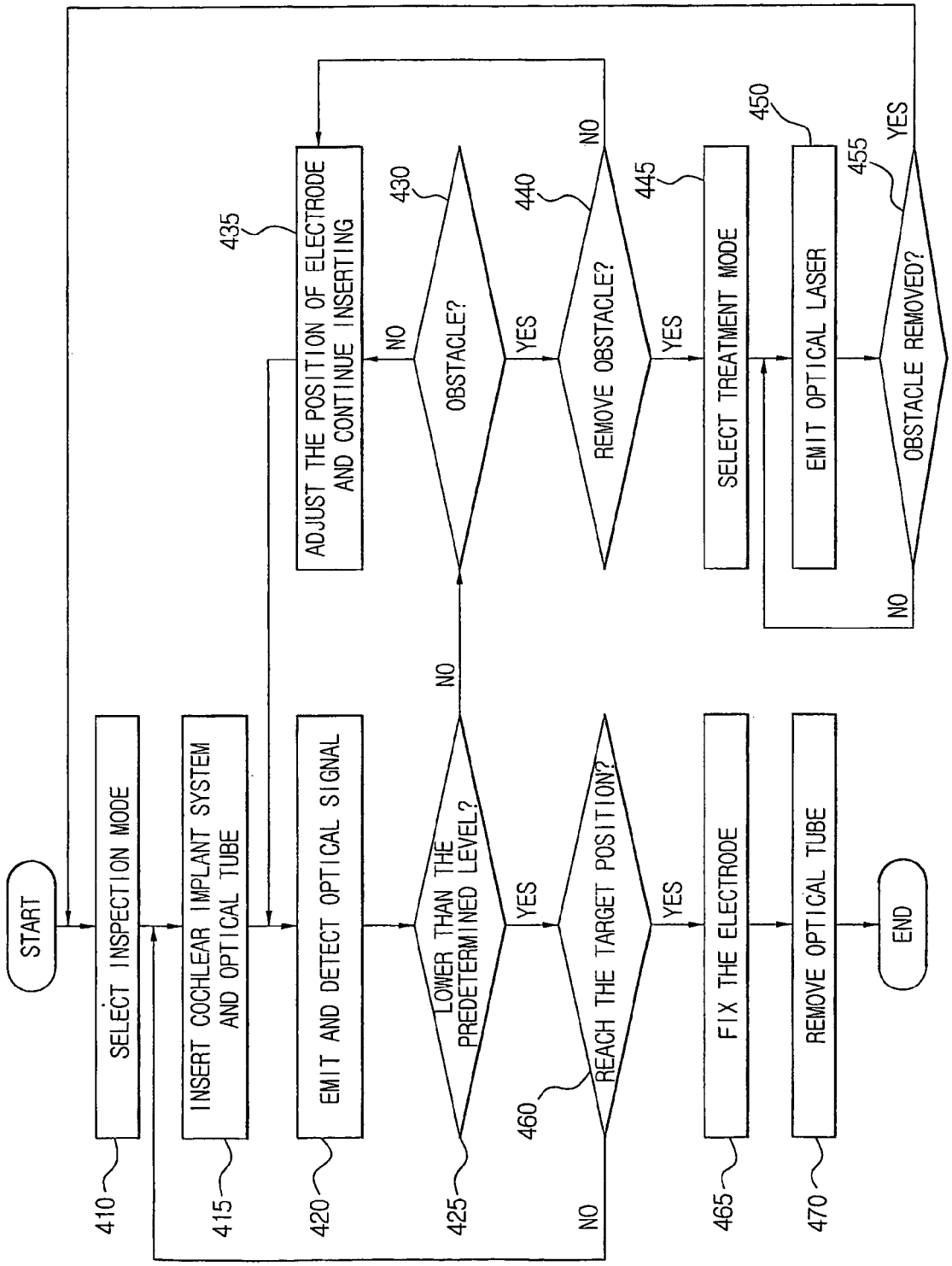
FIG. 4 is a flowchart showing the operation of guiding apparatus for cochlear implant according to one embodiment of the present invention.

FIG. 4 is a flowchart showing the operation of the guiding apparatus for cochlear implant according to one embodiment of the present invention.

Referring to FIG. 4, at step 410, the guiding apparatus for cochlear implant receives selection information for inspection mode from the surgeon. As already described above, the inspection mode is for detecting there is any obstacle on the inserting route of the electrode 110.

At step 415, the surgeon inserts the electrode 110 and the optical tube 340 through the inner ear of the patient.

During the insertion of the electrode 110 and the optical tube 340 at step 415, at step 420, the optical signal emitting module 325 emits the optical signal and the optical detecting module 330 detects the reflected optical signal under the control of central processor 310.

At step 425, the analysis processor 315 of the central processor 310 determines whether or not the amount of energy of optical signal that is detected by the optical signal detecting module 330 is lower than the predetermined value.

Namely, the analysis processor 315 compares the amount of optical emission energy of emitted optical signal and the amount of optical detection energy of detected optical signal to determine there is an obstacle or wall of cochlear ahead of the electrode 110 or optical tube 340, and analyzed data from the analysis processor 315 is displayed on the display 355.

If the amount of optical detection energy at step 425 is more than the predetermined value, the operation process proceeds to the step 430. At step 430, the surgeon can perceive there exist an obstacle ahead of electrode 110 or optical tube 340. If there is no obstacle, the surgeon adjusts the position of electrode and keeps inserting the electrode 110 at step 435. The operation process returns to the step 420.

But, if there exists an obstacle, the surgeon determines to remove the obstacle or not at step 440. If the surgeon determines not to remove it, then the operation process proceeds to the step 425. Otherwise, the surgeon selects the treatment mode at step 445.

At step 450, the optical signal emitting module 325 under the control of the optical signal magnitude switch 350 generates optical laser to remove the obstacle. That is, if the obstacle of structural or diseased cause is detected, the central processor 310 in the treatment mode amplifies the amplitude of beam to generate optical laser and burns out the obstacle by means of the optical laser.

At step 455, the surgeon can check that the removal of obstacle is accomplished from information displayed on display 355. If the obstacle is removed, then the operation process returns to the step 410; otherwise to the step 450.

If the amount of optical detection energy is lower than the predetermined value at step 425, the operation process proceeds to step 460. At step 460, the surgeon determines whether or not the electrode 110 reaches the target position on where it will be fixed. If it reaches the target position, the operation process proceeds to the step 465; Otherwise, the operation process returns to the step 415 to keep inserting the electrode 110 and the optical tube 340.

If the electrode 110 reaches to the target position, the surgeon can fix the electrode 110 at that position at step 465. Then, the electrode 110 is installed at that position by removing the optical tube 340 at step 470.

Although the flowchart in FIG. 4 includes the step of mode selection, the step 410 and step 445 can be omitted if both inspection mode and treatment mode can be performed at the default mode without mode change.

The operation process of the guiding apparatus for cochlear implant with reference to FIG. 4 describes the case that the optical tube 340 works as guiding wire 120, i.e., additional guiding wire is not required. But, it is also possible to use an electrode 120 with the guiding wire 10 and the optical tube 340 inserted therein. That is, the guiding wire 120 works for guiding and the optical tube 340 works for detecting and removing the obstacle on the inserting route respectively. If this guiding wire 120 is used, the step 470 in FIG. 4 is to remove the optical tube 340 and the guiding wire 120.

According to the guiding apparatus and method for cochlear implant that provides information of route and position to the surgeon, it is possible to decrease injuries to the inner wall of a cochlear canal and optimize the position of an electrode to be inserted into the cochlear canal.

Also, one embodiment of the invention can detect obstacles on the inserting route by use of the reflected optical signals and remove the detected obstacles by use of laser beam.

Furthermore, one embodiment of the invention can increase the accuracy and safety of operation by providing numerical and visualized information of the inserting process and route by use of optical signals.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

The invention claimed is:

1. A guiding apparatus for cochlear implant, which provides information on an inserting route of a cochlear implant system, comprising:
    at least one optical tube configured to transmit an optical signal toward the interior of an ear;
    an optical signal emitting module, coupled to one end of the at least one optical tube, configured to convert an electrical signal into the optical signal and emit the optical signal through another end of the optical tube;
    an optical signal detecting module, coupled to one end of the optical tube, configured to receive an optical signal that is reflected by an obstacle or an inner wall of a cochlear through another end of the optical tube and convert the received optical signal into an electrical signal;
    a processor configured to i) provide a control signal to the optical signal emitting module and the optical signal detecting module and ii) analyze optical emission energy information of the emitted optical signal and optical detection energy information of the converted electrical signal so as to generate inserting route information for the cochlear implant system, wherein the inserting route information comprises at least one of route information of an inner wall of a cochlear canal and position information of the optical tube;
    a display configured to output the generated inserting route information; and
    an optical signal magnitude switch configured to receive a command to control the magnitude of an optical laser beam to be emitted from the optical signal emitting module and configured to remove the obstacle,
    wherein the processor, in accordance to the command, is configured to control the optical signal emitting module so as to change the magnitude of the optical laser beam.

2. The guiding apparatus for cochlear implant of claim 1, wherein the processor comprises:
    an analysis processor configured to analyze the optical emission energy information and the optical detection energy information so as to generate the inserting route information of the cochlear implant system; and
    a transmittance controller configured to generate and transmit i) a control signal, which controls an amount of optical emission energy, to the optical signal emitting module and ii) a control signal, which controls the detection of an optical signal, to the optical signal detecting module.

3. The guiding apparatus for cochlear implant of claim 2, further comprising a contact switch configured to connect one end of the optical tube to one of the optical signal emitting module and the optical signal detecting module under the control of the transmittance controller in the case of one optical tube available.

4. The guiding apparatus for cochlear implant of claim 1, wherein the optical signal emitting module comprises:
    an amplifier configured to amplify the electrical signal in the form of a pulse received from the transmittance controller;
    a modulator configured to convert the amplified signal into the optical signal by use of an optical diode; and
    an illuminator configured to control a radiation angle of an optical signal by use of an optical device.

5. The guiding apparatus for cochlear implant of claim 1, wherein the optical signal detecting module comprises:
    a collector configured to detect the optical signal reflected by the inner wall of a cochlear canal or the obstacle by use of an optical detecting sensor;
    a converter configured to convert the detected optical signal into the electrical signal; and
    an amplifier configured to amplify the electrical signal to be sent to the processor.

6. The guiding apparatus for cochlear implant of claim 1, wherein the optical tube is formed of glass or plastic material.

7. The guiding apparatus for cochlear implant of claim 6, wherein the optical tube is shaped of a thin line.

8. The guiding apparatus for cochlear implant of claim 6, further comprising an electrode which is connected to the cochlear implant system and is inserted into a cochlear canal, wherein the electrode contains the optical tube.

9. The guiding apparatus for cochlear implant of claim 1, further comprising an electrode which contains the optical tube for working as a stylet for supporting the insertion of the electrode into the cochlear canal.

10. The guiding apparatus for cochlear implant of claim 1, wherein the optical tube works as an endoscope configured to detect an existence of an obstacle.

11. The guiding apparatus for cochlear implant of claim 1, further comprising an emission control switch configured to receive a command for selecting continuous emission or intermittent emission of the optical signal.

12. A guiding apparatus for cochlear implant, which provides information on an inserting route of a cochlear implant system, the apparatus comprising:
    at least one optical tube, configured to transmit an optical signal toward the interior of an ear;
    an optical signal emitter, coupled to one end of the at least one optical tube, configured to convert an electrical signal into the optical signal and emit the optical signal through another end of the optical tube;
    a detector configured to detect an optical signal that is reflected by a portion of the interior of the ear;
    a processor configured to provide inserting route information of the cochlear implant system based on the reflected optical signal, wherein the inserting route information comprises at least one of route information of an inner wall of a cochlear canal and position information of the optical tube; and
    an optical signal magnitude switch configured to receive a command to control the magnitude of an optical laser beam to be emitted from the optical signal emitter and configured to remove an obstacle,
    wherein the processor, in accordance to the command, is configured to control the optical signal emitting module so as to change the magnitude of the optical laser beam.

* * * * *